(12) United States Patent
Jackson et al.

(10) Patent No.: US 7,897,326 B2
(45) Date of Patent: Mar. 1, 2011

(54) PEROXISOME-PROLIFERATOR ACTIVATED RECEPTOR-ALPHA AGONISTS FOR ORGAN PRESERVATION

(75) Inventors: Travis Corey Jackson, Pittsburgh, PA (US); Zaichuan Mi, Wexford, PA (US); Edwin K. Jackson, Pittsburgh, PA (US)

(73) Assignee: University of Pittsburgh-of the Commonwealth System of Higher Education, Pittsburgh, PA (US)

( * ) Notice: Subject to any disclaimer, the term of this patent is extended or adjusted under 35 U.S.C. 154(b) by 496 days.

(21) Appl. No.: 11/687,419

(22) Filed: Mar. 16, 2007

(65) Prior Publication Data

US 2007/0218451 A1    Sep. 20, 2007

Related U.S. Application Data

(60) Provisional application No. 60/783,167, filed on Mar. 16, 2006.

(51) Int. Cl.
*A01N 1/02* (2006.01)
*A61K 31/7072* (2006.01)
*A61K 31/192* (2006.01)

(52) U.S. Cl. .............................. 435/1.1; 514/571; 514/49

(58) Field of Classification Search ........................ None
See application file for complete search history.

(56) References Cited

U.S. PATENT DOCUMENTS 5,834,178 A    11/1998    Churchill et al.
6,187,814 B1    2/2001    Elias et al.

FOREIGN PATENT DOCUMENTS

| EP | 0455042 A1 | * 11/1991 |
|---|---|---|
| EP | 1 621 200 A1 | 2/2006 |
| JP | 2004-339068 A | 12/2004 |
| WO | WO 02/34259 A1 | 5/2002 |
| WO | WO 03/059294 A2 | 7/2003 |
| WO | WO 03/075911 A1 | 9/2003 |
| WO | WO 2005/047268 A2 | 5/2005 |

OTHER PUBLICATIONS

Weiner et al (J Gen Intern Med. 2004; 19: 1045-1052).*
Kind et al. (Wisconsin Medical Journal. 2002; 101(7): 53-56).*
Jackson et al. (European Society for Organ Transplantation. 2007; 20: 277-290).*
International Search Report dated Mar. 26, 2008, in PCT/US2007/064198.
Jackson et al., *Transplant International*, 20: 277-290 (2007).

Muller et al., *American Journal of Pathology*, 164(2): 521-532 (Feb. 2004).
Written Opinion of the International Searching Authority dated Mar. 26, 2008, in PCT/US2007/064198.
Bastani et al., "Post-Transplant Hyperlipidemia: Risk Factors and Response to Dietary Modification and Gemfibrozil Therapy," *Clinical Transplantation*, 9: 340-348 (1995).
Bolz et al., "Intact Endothelial and Smooth Muscle Function in Small Resistance Arteries After 48 h in Vessel Culture," *American Journal of Physiology*, 279(3): H1434-H1439 (Sep. 2000).
Briére, "Human Foetal Kidney Explants in Serum-Free Organ Culture," *Anatomy and Embryology*, 176(1): 105-114 (1987).
Cerilli et al., "Effect of Mannitol, Saline, and Urea on the Function of a Recently Autotransplanted Kidney," *Archives of Surgery*, 92: 178-183 (Feb. 1966).
Chan et al., "Hyperlipidemia After Renal Transplantation: Treatment With Gemfibrozil," *Nephron*, 67(3): 317-321 (Jul. 1994).
Cuzzocrea et al., "Role of Endogenous and Exogenous Ligands for the Peroxisome Proliferators Activated Receptors Alpha (PPAR-α) in the Development of Inflammatory Bowel Disease in Mice," *Laboratory Investigation*, 84: 1643-1654 (2004).
Dishart et al., "An Evaluation of Pharmacological Strategies for the Prevention and Treatment of Acute Renal Failure," *Drugs*, 59(1): 79-91 (Jan. 2000).
Dubey et al., "Nitric Oxide Inhibits Angiotensin II-Induced Migration of Rat Aortic Smooth Muscle Cell," *The Journal of Clinical Investigation*, 96(1): 141-149 (Jul. 1995).
Dubey et al., "Smooth Muscle Cell-Derived Adenosine Inhibits Cell Growth," *Hypertension*, 27(No. 3, Pt. 2): 766-773 (Mar. 1996).
Dubey et al., "Exogenous and Endogenous Adenosine Inhibits Fetal Calf Serum-Induced Growth of Rat Cardiac Fibroblasts," *Circulation*, 96(8): 2656-2666 (Oct. 21, 1997).
Dubey et al., "Estrogen and Tamoxifen Metabolites Protect Smooth Muscle Cell Membrane Phospholipids Against Peroxidation and Inhibit Cell Growth," *Circulation Research*, 84(2): 229-239 (Feb. 5, 1999).
Dubey et al., "Methoxyestradiols Mediate the Antimitogenic Effects of Estradiol on Vascular Smooth Muscle Cells via Estrogen Receptor-Independent Mechanisms," *Biochemical and Biophysical Research Communications*, 278(1): 27-33 (Nov. 11, 2000).
Duez et al., "Regulation of Human ApoA-I by Gemfibrozil and Fenofibrate Through Selective Peroxisome Proliferator-Activated Receptor α Modulation," *Arteriosclerosis, Thrombosis, and Vascular Biology*, 25(3): 585-591 (Mar. 2005).
Fang et al., "Activation of Peroxisome Proliferator-Activated Receptor α by Substituted Urea-Derived Soluble Epoxide Hydrolase Inhibitors," *The Journal of Pharmacology and Experimental Therapeutics*, 314(1): 260-270 (2005).

(Continued)

*Primary Examiner* — Scott Long
(74) *Attorney, Agent, or Firm* — Leydig, Voit & Mayer, Ltd.

(57) ABSTRACT

Methods and compositions for reducing, preventing or reversing organ damage and/or enhancing organ preservation by administration of a peroxisome-proliferator activated receptor-alpha (PPARα) agonist to the organ.

31 Claims, 6 Drawing Sheets

OTHER PUBLICATIONS

Gao et al., "$\alpha_2$-Adrenoceptors Potentiate Angiotensin II- and Vasopressin-Induced Renal Vasoconstriction in Spontaneously Hypertensive Rats," *The Journal of Pharmacology and Experimental Therapeutics*, 305(2): 581-586 (2003).

Grino et al., "Flush Solution With Mannitol in the Prevention of Post-Transplant Renal Failure," *Transplantation Proceedings*, XIX(5): 4140-4142 (Oct. 1987).

Herrero et al., "Evaluation of a Preservation Solution Containing Fructose-1,6-Diphosphate and Mannitol Using the Isolated Perfused Rat Kidney, Comparison with Euro-Collins and University of Wisconsin Solutions," *Nephrology Dialysis Transplantation*, 10(4): 519-526 (1995).

Izzedine et al., "Renal Effects of PPAR$\alpha$-Agonists," *Minerva Urologica E Nefrologica*, 56(4): 339-342 (Dec. 2004).

Jackson et al., "Phosphodiesterases in the Rat Renal Vasculature," *Journal of Cardiovascular Pharmacology*, 30(6): 798-801 (Dec. 1997).

Jackson et al., "Modulation of Cyclic AMP Production by Signal Transduction Pathways in Preglomerular Microvessels and Microvascular Smooth Muscle Cells," *The Journal of Pharmacology and Experimental Therapeutics*, 310(1): 349-358 (Jul. 2004).

Jackson et al., "Mechanism of the Vascular Angiotensin II/$\alpha_2$-Adrenoceptor Interaction," *The Journal of Pharmacology and Experimental Therapeutics*, 314(3): 1109-1116 (Sep. 2005).

Jacobson et al., "Diuretics: Sites and Mechanisms of Action," *Annual Review of Pharmacology and Toxicology*, 16: 201-214 (1976).

Kasiske et al., "The Effects of Lipid-Lowering Agents on Acute Renal Allograft Rejection," *Transplantation*, 72(2): 223-227 (Jul. 27, 2001).

Kline et al., "High Osmolality-Low pH Flush Solutions Improve Renal Transplant Function in Rats," *Urological Research*, 19(2): 81-86 (1991).

Lane et al., "Effect of Mannitol and Polyethylene Glycol on the Action of Frusemide During Renal Storage and Transplantation," *Transplantation*, 62(5): 575-582 (Sep. 15, 1996).

Lopez-Costea et al., "Solucion De Manitol (M-400) Versus Solucion De Manitol Y Alopurinol En La Prevencion Del Fracaso Renal Agudo Post-TR," *Actas Urologicas Españolas*, 16(6): 446-450 (Jun. 1992).

Mi et al., "Metabolism of Exogenous Cyclic AMP to Adenosine in the Rat Kidney," *The Journal of Pharmacology and Experimental Therapeutics*, 273(2): 728-733 (May 1995).

Mi et al., "Evidence for an Endogenous cAMP-Adenosine Pathway in the Rat Kidney," *The Journal of Pharmacology and Experimental Therapeutics*, 287(3): 926-930 (Dec. 1998).

Mi et al., "Effects of $\alpha$- and $\beta$-Adrenoceptor Blockade on Purine Secretion Induced by Sympathetic Nerve Stimulation in the Rat Kidney," *The Journal of Pharmacology and Experimental Therapeutics*, 288(1): 295-301 (Jan. 1999).

Mouthiers et al., "Peroxisome Proliferator-Activated Receptor $\alpha$ Physically Interacts with CCAAT/Enhancer Binding Protein (C/EBP$\beta$) to Inhibit C/EBP$\beta$-Responsive $\alpha$1-Acid Glycoprotein Gene Expression," *Molecular Endocrinology*, 19(5): 1135-1146 (May 2005).

Nissenson et al., "Mannitol," *The Western Journal of Medicine*, 131(4): 277-284 (Oct. 1979).

Nydegger et al., "New Concepts in Organ Preservation," *Transplant Immunology*, 9: 215-225 (2002).

Ren et al., "PPAR$\alpha$ Activation Upregulates Nephrin Expression in Human Embryonic Kidney Epithelial Cells and Podocytes by a Duel Mechanism," *Biochemical and Biophysical Research Communications*, 338(4): 1818-1824 (Dec. 30, 2005).

Strakova et al., "Peroxisome Proliferator-Activated Receptors (PPAR) Agonists Affect Cell Viability, apoptosis and Expression of Cell Cycle Related Proteins in Cell Lines of Glial Brain Tumors," *Neoplasma*, 52(4): 126-136 (2005).

Tiggeler et al., "Prevention of Acute Tubular Necrosis in Cadaveric Kidney Transplantation by the Combined Use of Mannitol and Moderate Hydration," *Annals of Surgery*, 201(2): 246-251 (Feb. 1985).

Töröner et al., "Effects of PPAR$\gamma$ and PPAR$\alpha$ Agonists on Serum Leptin Levels in Diet-Induced Obese Rats," *Hormone and Megabolic Research*, 36: 226-230 (Apr. 2004).

Van Raalte et al., "Peroxisome Proliferator-Activated Receptor (PPAR)-$\alpha$: A Pharmacological Target with a Promising Future," *Pharmaceutical Research*, 21(9): 1531-1538 (Sep. 2004).

Vergoulas et al., "Combined Treatment of Hypercholesterolemia of Renal Transplant Allograft Recipients with Fluvastatin and Gemfibrozil," *Transplant International*, 13(Suppl 1): S64-S67 (2000).

Vyas et al., "The Inhibitory Effect of Angiotensin II on Stimulus-Induced Release of cAMP Is Augmented in the Genetically Hypertensive Rat Kidney," *The Journal of Pharmacology and Experimental Therapeutics*, 279(1): 114-119 (Oct. 1996).

Weimar et al., "A Controlled Study on the Effect of Mannitol on Immediate Renal Function After Cadaver Donor Kidney Transplantation," *Transplantation*, 35(1): 99-101 (Jan. 1983).

Zacharia et al., "Methylation of 2-Hydroxyestradiol in Isolated Organs," *Hypertension*, 42: 82-87 (Jul. 2003).

\* cited by examiner

A # PEROXISOME-PROLIFERATOR ACTIVATED RECEPTOR-ALPHA AGONISTS FOR ORGAN PRESERVATION

CROSS-REFERENCE TO RELATED APPLICATIONS

This patent application claims the benefit of U.S. Provisional Patent Application No. 60/783,167, filed Mar. 16, 2006, which is incorporated herein in its entirety.

BACKGROUND OF THE INVENTION

The era of modern pharmacology has ushered in a wealth of drugs that selectively modulate molecular systems within cells, tissues and organs. However, despite the sheer number of drugs/drug classes now available, very few pharmacological agents are known to be effective in organ preservation solutions.

The identification of drugs that preserve organs has enormous implications for progress in medicine. For example, effective drugs that can be added to organ preservation solutions, such as University of Wisconsin solution, Celsior solution, St. Thomas Hospital 2 solution, Ringer-lactate solution, Euro-Collins solution or Bretschneider HTK solution could extend the time for extracorporeal survival of grafts prior to transplantation, decrease the incidence of primary graft dysfunction and delayed function and augment the pool of available donors. Preserving drugs could be delivered to the organ while still in the donor (in situ) or instilled into the organ after removal from the donor (in vitro). In addition to or instead of adding preserving drugs to a preservation solution, the drugs may be administered to the organ donor before removal of the organ (in vivo) or to the organ recipient (in vivo) before or just after transplant. Moreover, such drugs may find utility for the prevention and treatment of acute organ failure, for example acute renal failure for which no effective pharmacological agent is currently known. Furthermore, protecting drugs, if sufficiently efficacious, may allow for the prolonged in situ perfusion of organ systems with solutions to restore organ function and/or to selectively deliver other drugs or molecular biological constructs (e.g., plasmids, viral vectors, siRNAs, anti-sense oligonucleotides) directly to the target organ.

Accordingly, there is a desire in the art for methods and compositions for reducing, preventing or reversing organ damage or enhancing organ preservation.

BRIEF SUMMARY OF THE INVENTION

The present invention relates to methods and compositions for reducing, preventing or reversing organ damage or enhancing organ preservation. In particular, the present invention relates to methods and compositions for reducing, preventing or reversing organ damage or enhancing organ preservation by administration of a peroxisome-proliferator activated receptor-alpha (PPARα) agonist. The organ may be a kidney, liver, skin, heart or lung.

In one embodiment, the present invention is directed to a method for preventing, reducing or reversing organ damage and/or enhancing a organ preservation comprising contacting the organ with a PPARα agonist. In a still further embodiment the method further comprises contacting the organ with a cell-impermeable solute.

In another embodiment, the present invention is directed to a method for preventing, reducing or reversing a organ damage and/or enhancing a organ preservation comprising contacting the organ with a preservation solution wherein the preservation solution comprises a PPARα agonist. The preservation solution may further comprise a cell-impermeable solute.

In yet another embodiment, the present invention is directed to a composition for preventing, reducing or reversing organ damage and/or enhancing organ preservation comprising a PPARα agonist.

DETAILED DESCRIPTION OF THE INVENTION

Figure 1:
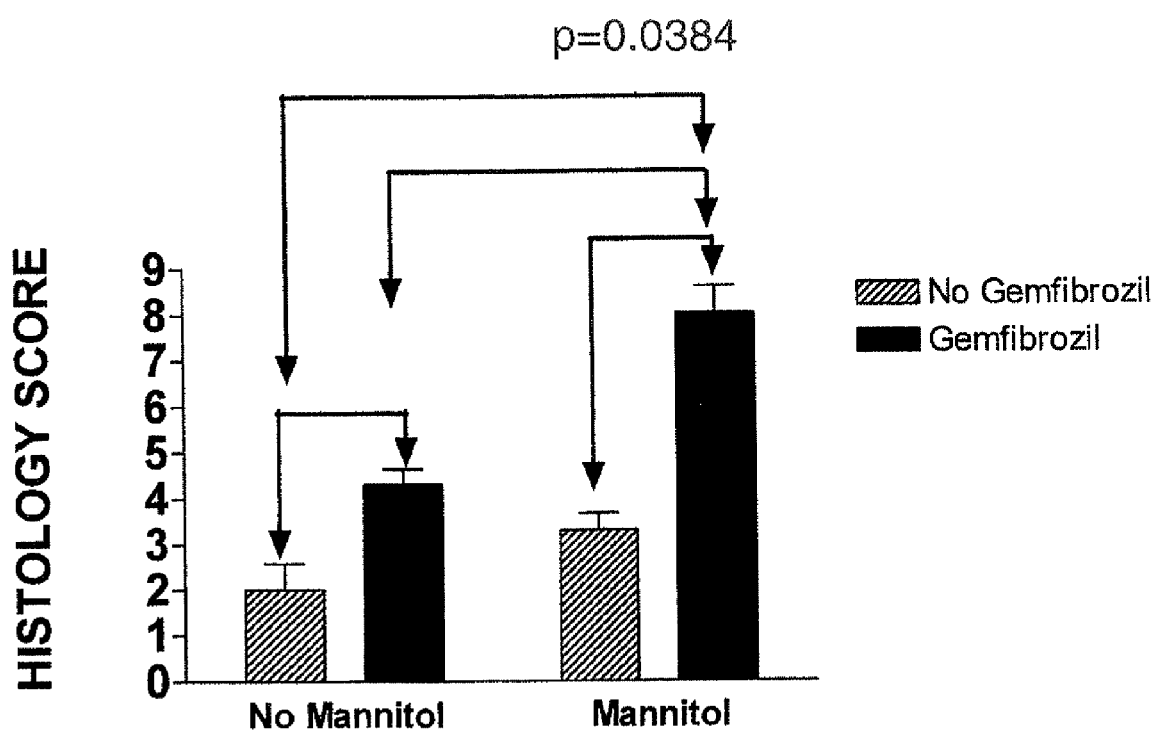
FIG. 1 is a graph of the histology score for control kidney and kidney exposed to mannitol, gemfibrozil, or mannitol+gemfibrozil.

The present invention relates to methods and compositions for reducing, preventing or reversing organ damage or enhancing organ preservation. In particular, the present invention relates to methods and compositions for reducing, preventing or reversing organ damage or enhancing organ preservation by administration of a peroxisome-proliferator activated receptor-alpha (PPARα) agonist. In one embodiment, the invention is directed to methods for reducing, preventing or reversing organ damage and/or enhancing organ preservation by contacting the organ with a peroxisome proliferator activated receptor-alpha (PPARα) agonist in an amount sufficient to reduce, prevent or reverse organ damage or enhance organ preservation.

The organ may be any organ, such as a kidney, liver, heart, lung, skin, or pancreas. Preferably, the organ is a kidney, heart, liver or lung.

PPARα is a ligand-activated transcriptional factor that is a member of the nuclear receptor family (see e.g., van Raalte, *Pharm Res.*, 21:1531 (2004)). PPARα modulates the expression of multiple genes that participate in fatty acid metabolism including fatty acid transport protein, actyl-coA synthetase, fatty acid binding protein, medium chain acyl-coenzyme A dehydrogenase, acyl-coA oxidase, cytochrome P450 fatty acid ω-hydroxylase and carnitine palmitoyl transferase I (see e.g., van Raalte, *Pharm Res.*, 21:1531 (2004)). PPARα agonists also increase the expression of nephrin by glomerular podocytes. (see e.g., Ren, *Biochem. Biophys. Res. Commun.*, 338:1818 (2005)).

According to one embodiment, the present invention provides a composition (i.e., a preservation solution) for preventing, reducing or reversing organ damage or enhancing organ preservation comprising a PPARα agonist. The composition may additionally comprise a cell-impermeable solute.

According to another embodiment, the present invention provides a method for preventing, reducing or reversing organ damage and/or enhancing organ preservation comprising contacting the organ with a PPARα agonist.

Any member of the pharmacological class of PPARα agonists may be used according to the present invention. For example, the PPARα agonists may be selected from the members of the fibric acid class of PPARα agonists (e.g., gemfibrozil, clofibrate, fenofibrate, ciprofibrate, and bezafibrate). In preferred embodiments, the PPARα agonist is gemfibrozil or 4-chloro-6-(2,3-xylidino)-2-pyrimidinylthioacetic acid (WY-14643).

In further embodiments, the present invention additionally comprises contacting an organ with a cell-impermeable solute. Any cell-impermeable solute known in the art, especially those that have been used clinically, may be used according to the present invention. Cell-impermeable solutes include, inter alia, mannitol, glycerin, isosorbide, urea, lactate, raffinose, hydroxyethyl starch, glucose, University of Wisconsin solution, Celsior solution, St. Thomas Hospital 2 solution, Ringer-lactate solution, Euro-Collins solution or Bretschneider HTK solution. Preferably, the cell-impermeable solute is mannitol. The cell impermeable solute may be administered prior to, concurrently with, or following the administration of the PPARα agonist.

The amount of the PPARα agonist in the preservation solution will depend on the potency of the particular drug. In preferred embodiments, the concentration of the PPARα agonist is present in an amount that activates the nuclear receptor PPARα in the organ. Generally, the PPARα agonist is present in an amount ranging from 1 nanogram/liter to 100 grams/liter. When used, the amount of the cell-impermeable solute in the preservation solution depends on the molecular weight of the cell-impermeable solute. In preferred embodiments, the cell-impermeable solute is present in a concentration that causes redistribution of water across cell membranes of the organ. Generally, the cell-impermeable solute is present in an amount ranging from 1 millimole/L to 1000 millimoles/L.

The organ may be contacted with (or administered) the preservation solution comprising the PPARα agonist alone or in combination with the cell-impermeable solute, by having it flushed, continuously perfused, or intermittently perfused through the blood vessels of the organ while the organ is still in a subject's body, during the removal of the organ from a subject's body, after the organ is removed from a subject's body, while the organ is being transplanted into a recipient, immediately after the organ is transplanted into a recipient, and combinations thereof. In one embodiment, the organ preservation solution comprising the PPARα agonist alone or in combination with the cell-impermeable solute is administered directly into the organ's blood supply while the organ is being blood-perfused by a cardiovascular system, which can be within the body of the organ donor or organ recipient.

Routes of administration include, but are not limited to, oral, intravenous injection or infusion, intra-arterial injection or infusion, subcutaneous injection, intra-muscular injection, rectal, percutaneous, nasal or pulmonary. In addition, the organ preservation solution comprising the PPARα agonist alone or in combination with the cell-impermeable solute may be placed around the immediate environment of the organ in vitro or in vivo or in situ or ex vivo.

The use of PPARα agonists in combination with cell-impermeable solutes provides a synergistic effect as compared to the use of either alone. The administration of a PPARα agonist to organ preservation solutions, alone or in combination with cell-impermeable solutes, may extend the time for extracorporeal survival of grafts prior to transplantation, decrease the incidence of primary graft dysfunction and delayed function and augment the pool of available donors.

Because PPARα agonists synergize with cell-impermeable solutes, the benefit derived from the addition of PPARα agonists to preservation solutions that contain mannitol, such as Celsior and Bretschneider HTK solutions (see e.g., Nydegger, Transpl. Immunol., 9:215 (2002)) may be particularly efficacious. Moreover, in recent years, innovative devices, such as the Life Port® Transporters developed by Organ Recovery Systems (Des Plaines, Ill.), which provide constant, normothermic perfusion of organs during transport to the organ recipient have been developed. Addition of PPARα agonists to the solutions of such systems may increase the recovery of organs from marginally acceptable donors and thereby expand the available supply of organs for transplantation.

The following examples are merely illustrative of the present invention and should not be construed as limiting the scope of the invention in any way as many variations and equivalents that are encompassed by the present invention will become apparent to those skilled in the art upon reading the present disclosure.

Example

Animals. Male Sprague-Dawley rats, 15 to 20 weeks-of-age, were housed in a University of Pittsburgh Medical Center animal care facility (temperature 22 EC; light cycle 12 hours; relative humidity 55%). Animals were fed Pro Laboratory RMH 3000 rodent diet (PMI Nutrition Inc., St. Louis, Mo.) and were given water ad libitum. Institutional guidelines for animal welfare were followed, and the Institutional Animal Care and Use Committee approved experimental protocols.

Preparation of Perfusion System. Due to bacterial infection associated with chronic kidney perfusion at 37° C., rat kidneys were perfused in a sterile environment. A glass perfusion system (Hugo Sachs Elektronik-Harvard Apparatus GmbH), which allowed for autoclaving and ultraviolet-light sterilization without damage to the structural integrity of the system, was used in all experiments. This system included the following components arranged in series: a jacketed glass perfusate reservoir for warming and initial oxygenation of perfusate; a jacketed glass-oxygenator for additional oxygenation; a Windkessel chamber for absorption of pulsations; a jacketed heat exchanger for warming the perfusate and trapping bubbles just before the perfusate enters the kidney; and a jacketed organ chamber to keep the kidney's surrounding environment at 37° C.

This system was modified in five ways. First, the Plexiglas framework that came with the system was eliminated and replaced with a custom-built aluminum framework that could withstand ultraviolet irradiation (University of Pittsburgh Department of Pharmacology Machine Shop). Second, the plastic inline filter holder that came with the system was eliminated and replaced with two high-pressure stainless steel filter holders (filter diameter, 47 mm; filtration area, 11.2 $cm^2$; catalog number, c-06644-50; Cole-Palmer, Vernon Hills, Ill.) that could be autoclaved and that provided a greater surface area for filtration (to prevent back-pressure) and that were configured in parallel (also to reduce back-pressure) between the oxygenator and Windkessel. The female fittings that screwed into each end of the body of the stainless steel filter holders leaked after repeated autoclaving, so these fittings were custom welded to the filter body (Department of Pharmacology Machine Shop). Third, the tubing that came with the system that connected the glass components was discarded and replaced with Tygon® Norprene® tubing (catalog number 72-0948; Harvard Apparatus, Holliston, Mass.) that could withstand repeated autoclaving. Fourth, a small plastic platform was inserted into the organ chamber upon which the kidney rested to prevent kinking of the renal artery and ureter. Fifth the various sections of tubing were either connected with plastic male Luer adapters (Harvard Apparatus) or metal stopcocks (Harvard Apparatus) or disposable plastic stopcocks (Cole-Palmer). The perfusate was pumped with a roller pump (model ISM834A, Ismatec, Glattbrug-Zurich, Switzerland), and the aforementioned jacketed devices were maintained at 37° C. with a thermostatic circulator (model 1136, VWR Scientific, Niles, Ill.). Tygon roller pump tubing (Harvard Apparatus) was used to pump perfusate from the reservoir toward the oxygenator (catalog number 731839), from the overflow of the oxygenator back toward the reservoir (catalog number 730155), from the main outflow of the oxygenator toward the Windkessel (catalog number, 731836), and from the organ chamber back toward the reservoir (catalog number 730155).

In preparing for kidney isolation, surgical tools, paper towels to drape the animal, gauze, surgical sutures and swabs were wrapped in surgical towels. Next the perfusion apparatus was entirely dismantled, and glass components, tubing, metal filter holders (fitted with glass fiber filters, size 0.7 micron, catalog number GF7547MM; Advantec MFS, Inc., Pleasanton, Calif.), tubing connectors and stopcocks were also placed in surgical towels. The surgical towels were placed in a metal tray, which was wrapped in a surgical blanket and placed in an autoclave for 35 minutes at 135 EC. While the instruments, surgical supplies and system were being sterilized, the laminar flow hoods were cleaned with 75% alcohol and irradiated with ultraviolet light. Following sterilization of both instruments and hoods, the perfusion apparatus was reassembled in the large SG-400 hood. New (disposable) plastic 4-way connectors were placed where necessary and other connectors were applied appropriately for the perfusion apparatus to work properly. The kidney perfusion system was then flushed with filtered (0.22 microns) de-ionized water to remove any particles or residue that may have been deposited during the previous experiment. The autoclaved instruments and surgical supplies were placed in the second laminar flow hood (catalog number 3740002; Labconco, Kansas City, Mo.).

Drug Preparation. Leibovitz L-15 cell culture medium (Sigma, St. Louis, Mo.) was mixed according to the manufacture's specifications to make 2 liters and 120 mg of penicillin was added. The pH of one liter of L-15 was adjusted to 7.4, and this solution was used during the kidney isolation procedure. The other liter was further prepared with addition of various pharmacological agents, and then the pH adjusted to 7.4. Both solutions were then filtered (0.22 microns) into 1 liter containers. The solution with the experimental drug was then perfused through the kidney perfusion system at a rate of 2.6 ml/min. The other solution was placed underneath the hood where the surgery was to be done.

Kidney Isolation. Kidneys were isolated under a laminar flow hood (Labconco) fitted with a separate roller pump. The operator used sterilized latex gloves with frequent application of 75% alcohol to gloves and instruments throughout the course of the surgery. Gloves were replaced anytime the operator's hands left the surgical hood. Animals were anesthetized with Inactin (90 mg/kg, ip; Sigma), the abdomen was shaved, washed with 75% alcohol, and covered with autoclaved paper towels. The tubing, which would eventually be required for isolation, was assembled and placed in the roller pump. This tubing consisted of three sequentially smaller sections, the middle of which was the pump tubing (Harvard Apparatus). The smallest of the sections was linked, using an adaptor connector, to PE-50 tubing (which had been previously soaked in alcohol for at least 2 days). This PE-50 tubing was for insertion into the renal artery. The largest size tubing was placed into the 1 liter of room temperature L-15. The pump was turned on for a brief time, allowing all tubing to be filled with L-15 medium to remove all air bubbles from the tubing. The skin covering the abdominal cavity was cut horizontally. A light spray of alcohol was applied to the area to remove pieces of hair, followed by a horizontal cut in the same area through the muscle; exposing the internal organs. A section of sterile gauze was set to the left of the animal, and the large/small intestines were gently pulled out of the abdominal cavity and wrapped in the gauze. This revealed the animal's left kidney, and the ureter was gentle cleaned and cannulated with a short section of PE-10 tubing connected to a longer section of PE-50 tubing (all presoaked in alcohol). All side branches of the renal artery and vein were ligated and cut. Next, the aorta, vena cava, renal artery and renal vein were identified, cleaned of fat and connective tissue and dissected free, and ligatures were loosely placed around these vessels. The infra-renal aorta was ligated, a small clamp was placed on the aorta just above the ligation but below the renal artery, a cut was made between the clamp and ligation, and the PE-50 tubing was inserted, secured with a ligature and advanced into the left renal artery. At this point the roller pump was turned on to perfuse the kidney with room temperature L-15 at 5 ml/min. The supra-renal aorta and renal vein were immediately ligated and severed. Next, the kidney, now completely isolated from the cardiovascular system of the animal, was freed from surrounding tissue, placed in sterile saline solution in a sterilized Petri dish, and transferred to the perfusion apparatus within seconds of interrupting flow. Adjusting the position of the kidney on the plastic sterilized platform prevented any kinking of the renal artery. The ureter catheter was directed to a urine collection system. The kidney was then perfused for 12 hours at 37° C. with L-15 gassed with 100% oxygen. Throughout the 12-hour experiment, perfusion pressure was time-averaged every 5 minutes using a Digi-Med (Louisville, Ky.) model BPA digital pressure measuring system, and pressure data were captured with a computer running the Digi-Med software package.

Collection of Kidneys. A timed urine collection was performed at the beginning and end of each perfusion experiment, and urine was also collected throughout the 12 hours of perfusion. After 12 hours, the kidney was removed and rapidly sectioned into three pieces. One piece was placed in 10% buffered formalin for light microscopy and Apoptag staining, another slice was placed in Karnovsky's fixative for electron microscopy, and the third section was rapidly frozen and stored at −80 EC for Western blot analysis.

Light Microscopy. The portion of kidney stored in 10% buffered formalin was processed and embedded in paraffin. Two-micron thick sections were cut and stained with hematoxylin-eosin, periodic acid-Schiff and methenamine silver-trichrome stains. Specimens were examined on a Nikon 50i compound microscope, and images were captured using a color digital camera (RT-KE Slider F Mount Camera) that was controlled by a computerized imaging system (SPOT RT-RE Camera Controller and Board) (all microscope and accessories from Fryer Company, Huntley, Ill.).

Electron Microscopy. Separate 1 $mm^3$ pieces of fresh rat kidney tissue were placed in Karnovsky's fixative (paraformaldehyde/glutaraldehyde), rinsed in buffer, post-fixed in osmium tetroxide, processed and embedded in Epon. Thin sections were cut on copper grids using an ultramicrotome, stained with uranyl acetate and lead citrate and examined with a FEI/Philips CM12 electron microscope (Eindhoven, The Netherlands). Digital images were obtained using an AMT digital camera (Danvers, Mass.).

Apoptag Staining. Five-micron sections were cut from the paraffin-embedded tissue blocks, and these sections were heated in an oven (55-58° C. for 45 minutes), deparaffinized and hydrated. A commercial ApopTag Peroxidase In Situ Apoptosis Detection Kit (Chemicon International, Temecula, Calif.) was used to detect apoptotic cells. Detection of apoptosis is based on the TUNEL method and the use of an anti-digoxigenin antibody that is conjugated to a peroxidase reporter molecule in accordance with the manufacturer's direction. Apoptotic cells showed brown nuclear staining on microscopic examination.

Western Blotting. Tissues were homogenized in lysis buffer (Tris HCl, 2% SDS, glycerol, phenylmethylsulphonylfluoride and protease inhibitors). Protein concentrations were measured using the BCA protein assay kit (Pierce Biotechnology, Inc., Rockford, Ill.). Whole homogenates proteins were solubilized at 60° C. for 15 min in Laemmli sample buffer. Sodium dodecyl sulphate-polyacrylamide gel electrophoresis (SDS-PAGE) was performed on gradient polyacrylamide gels (4-12%) loaded with 20 μg protein per lane. For immunoblotting, proteins were transferred electrophoretically to polyvinylidene fluoride (PVDF) membranes. Membranes were blocked in 5% milk for 2 hours, probed overnight at 4° C. with primary antibody (anti-$Na^+$—$K^+$-ATPase-$\alpha_1$, 1:5000, Chemicon, Temecula, Calif.) in phosphate-buffered saline (PBS) containing 1% milk. Membranes were probed with anti-β-actin (1:10,000, Sigma) for 1 hour to determine loading efficiency. Subsequently, membranes were exposed to a secondary horseradish peroxidase (HRP)-conjugated donkey anti-rabbit polyclonal antibody (1:5000, Pierce Biotechnology Inc., Rockford, Ill.) in PBS containing 1% milk for 1 hour at room temperature. Bound antibodies were visualized using a luminol-based enhanced chemiluminescence substrate (SupersignalWest Dura Extended Duration Substrate, Pierce) before exposure to X-ray film (Kodak 165-1579; Eastman Kodak Co., Rochester, N.Y.). Densitometric analysis was performed using ImageQuant TL (Amersham Biosciences, Piscataway, N.J.) and band densities were normalized to β-actin.

Statistics. Data were analyzed with a 1-factor or 2-factor analysis of variance using NCSS 2004 statistical package (Kaysville, Utah). $P<0.05$ was the criterion of significance.

Results. As a point of reference, some kidneys were not perfused chronically but were only briefly perfused (30 minutes) with L-15 and then processed for light microscopy. Twelve-hour perfusion (37° C. with L-15 gassed with 100% oxygen) resulted in nearly complete destruction of the renal architecture. Bowman's space and the glomerular capillary loops were collapsed and/or filled with an amorphous substance, the tubules were fragmented and occluded with cellular debri/casts, tubular epithelial cells were detached from basement membrane, nuclei were pyknotic and the interstitial space was edematous.

To identify pharmacological agents that would be useful for organ preservation, a number of pharmacological agents were screened: decylubiquinone (mitochondrial transition pore inhibitor); Z-VAD (caspase inhibitor); gemfibrozil and WY-14643 (PPARα agonists); trolox, luteolin and quercetin (antioxidants); hepatocyte growth factor, platelet-derived growth factor, epidermal growth factor and transferrin (growth factors); Z-Val-Phe-CHO (calpain inhibitor); W7 (calmodulin inhibitor); minoxidil and its active metabolite, minoxidil sulfate ($K_{ATP}$ openers); 3-aminobenzamide (inhibitor of poly(ADP-ribose)polymerases); verapamil (calcium channel blocker); DDAVF (selective $V_2$ agonist); acetazolamide, hydrochlorothiazide and furosemide (diuretics); mannitol (cell-impermeable solute); L-16504 (PPARβ agonist); dopamine (dopamine receptor agonist dopamine); linolenic acid (essential fatty acid); β-NAD (involved in energy metabolism); uric acid (normally exists in high concentrations in renal interstitium); and insulin, hydrocortisone, thyroid hormone and aldosterone (hormones). Only the PPARα agonists and mannitol provided moderate histological preservation as assessed by light microscopy. Aldosterone, uric acid, 3-aminobenzamide and minoxidil sulfate demonstrated mild protection. The remaining agents either had no effect or worsened the histological outcome.

The efficacy of mannitol combined with a PARRα agonist was also investigated. Accordingly, 12 kidneys were randomized for treatment with either L-15 alone (damaged control) or L-15 containing either mannitol (20 grams/L; Sigma), gemfibrozil (50 mg/L; Sigma) or gemfibrozil (50 mg/L) plus mannitol (20 grams/L). These kidneys were perfused as described above and processed for light microscopy, electron microscopy, Apoptag staining and Western blotting. An additional three kidneys were treated with WY-14643 (16 mg/L; Biomol, Plymouth Meeting, Pa.) and examined by light microscopy only.

Twelve hours of perfusion obliterated the glomerular, tubular and interstitial renal architecture in all three kidneys perfused with L-15 alone. At the light microscopic level, histology was modestly improved by mannitol or gemfibrozil alone, but was markedly improved by the combination of gemfibrozil plus mannitol. In this regard, in the kidneys treated with the combination, Bowman's space and capillary lumens were observable, tubules were mostly intact, few epithelial cells were detached from the underlying basement membrane, cells appeared less pyknotic and the interstitium contained much less edema.

To semi-quantify the protective effects of mannitol, gemfibrozil and gemfibrozil plus mannitol, a histology scoring system was devised in which 0 represented histological damage that was so severe that the micro-structure was unrecognizable and 10 represented the histology evident in a 30-minute flushed kidney. A score was then assigned by a blinded observer that considered the extent and severity of all of the aforementioned histopathology. As shown in FIG. 1, mannitol's effect per se did not achieve statistical significance. However, gemfibrozil statistically significantly improved the histological score in both non-mannitol-treated and mannitol-treated kidneys. However, the effects of gemfibrozil were statistically significantly greater in mannitol-treated kidneys than in non-mannitol-treated kidneys (arrows connect statistically significantly different groups ($p<0.05$ Fisher's Least Significant Difference test); P-value at top of figure is for interaction term in 2-factor analysis of variance).

Four kidneys, one from each group, were randomly selected for electron microscopic studies. At the electron microscopic level, in the L-15 alone kidney, Bowman's space was filled with cellular detritus, capillary loops were obliterated, and visceral epithelial cells were absent. Glomerular ultrastructure appeared slightly improved in both the mannitol-treated and gemfibrozil-treated kidneys, and was markedly improved in the mannitol plus gemfibrozil-treated kidney. The combination treatment resulted in many glomeruli with open capillaries, a Bowman's space with little cellular detritus, a covering of visceral epithelial cells, unfragmented podocytes with foot processes extending to the glomerular basement membrane and endothelial cells with large non-condensed nuclei.

The proximal tubular epithelial structures were destroyed by 12 hours of perfusion with L-15 alone. In this regard, no brush border was evident, tubular epithelial cells were unrecognizable and the tubular lumen was filled with amorphous casts. This severe histopathology was evident throughout the observed section, with no areas showing preservation. Tubular ultrastructure was only marginally better in mannitol-treated and gemfibrozil-treated kidneys. Notably, in the gemfibrozil plus mannitol-treated kidney, ultrastructure was highly preserved in many tubules. Proximal tubular epithelial cells with normal brush border and tight junctions, large and numerous mitochondria and a normal basement membrane were evident.

Figure 2:
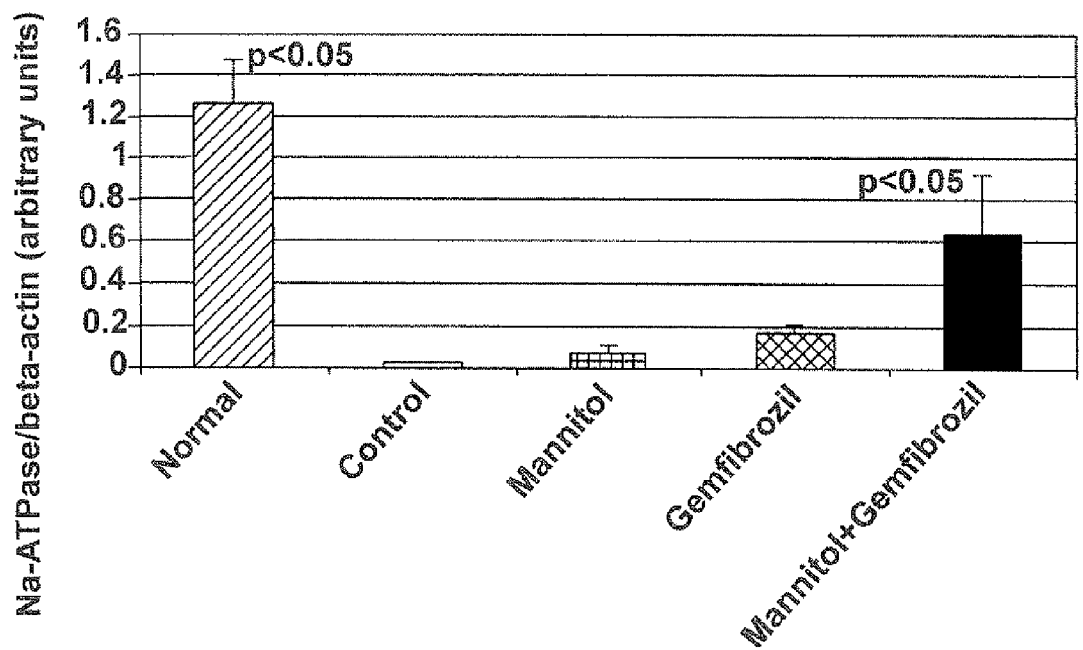
FIG. 2 is a graph of the Na—K-ATPase/beta-actin level in normal, control, and mannitol, gemfibrozil and mannitol+gemfibrozil treated kidney tissue.

The light and electron microscopic images provided supporting evidence for preservation by gemfibrozil, particularly when combined with mannitol. To further test the hypothesis of gemfibrozil-induced preservation, Western blotting and densitometry were used to examine the expression of $Na^+$—$K^+$-ATPase-$\alpha_1$. $Na^+$—$K^+$-ATPase provides the driving force for tubular reabsorption in renal epithelial cells and therefore is richly expressed in the basolateral membrane of all renal epithelial cells. Damage of epithelial cells would be expected to be associated with a reduction in the expression of this protein. As shown in FIG. 2, $Na^+$—$K^+$-ATPase-$\alpha_1$ was strongly expressed in normal (freshly isolated) kidneys ($p<0.05$ indicates that group is statistically significantly different from control, mannitol and gemfibrozil groups (Fisher's Least Significant Difference test)). However, $Na^+$—$K^+$-ATPase-$\alpha_1$ expression was nearly undetectable in kidneys perfused with L-15 alone and in mannitol-treated kidneys, but was slightly higher in gemfibrozil-treated kidneys. Importantly, $Na^+$—$K^+$-ATPase-$\alpha_1$ was statistically significantly greater in gemfibrozil plus mannitol-treated kidneys compared with kidneys treated with L-15 alone, mannitol alone or gemfibrozil alone. These objective results were consistent with the subjective histological analysis.

Figure 3:
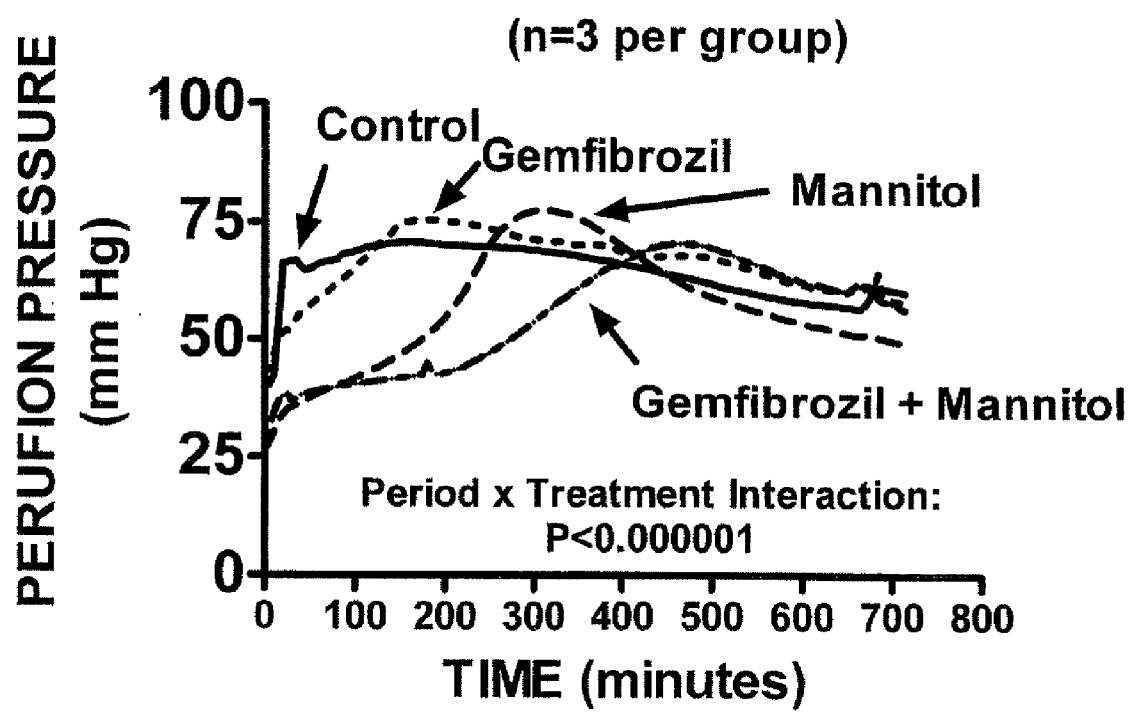
FIG. 3 is a graph of perfusion pressure over time in control and tissue exposed to gemfibrozil, mannitol and mannitol+gemfibrozil.

In the model system used in to exemplify the present invention, renal perfusion flow rate was low, but within the normal limits for an adult rat. This lower flow rate allowed the addition of mannitol to the L-15 without unacceptable back-pressure behind the 0.7 micron inline filters. Because of the low flow rate and low viscosity of L-15 relative to blood, the initial perfusion pressure in L-15 alone kidneys was approximately 50 mm Hg, increased rapidly and within 30 minutes to approximately 65 mm Hg, and thereafter changed little (FIG. 3). In kidneys receiving mannitol, either alone or with gemfibrozil, initial renal perfusion pressure was lower (approximately 25 mm Hg). The rapid increase in perfusion pressure observed in L-15 alone kidneys was delayed by gemfibrozil, more so by mannitol and even more by the combination of gemfibrozil with mannitol (FIG. 3).

Figure 4A:
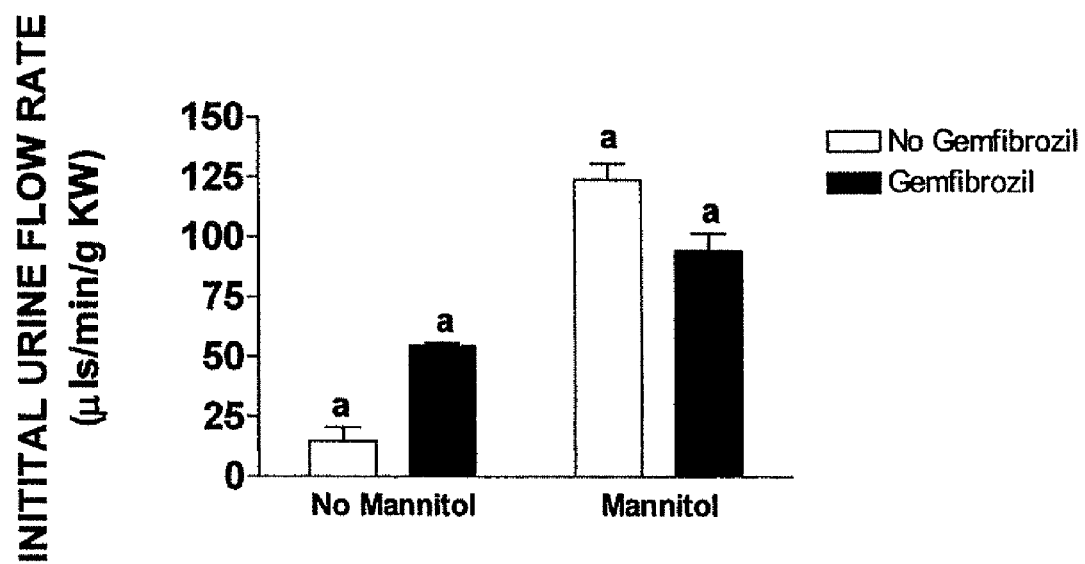
FIG. 4A is a graph of initial urine flow rate in control kidney and kidney exposed to mannitol, gemfibrozil, or mannitol+gemfibrozil.
Figure 4B:
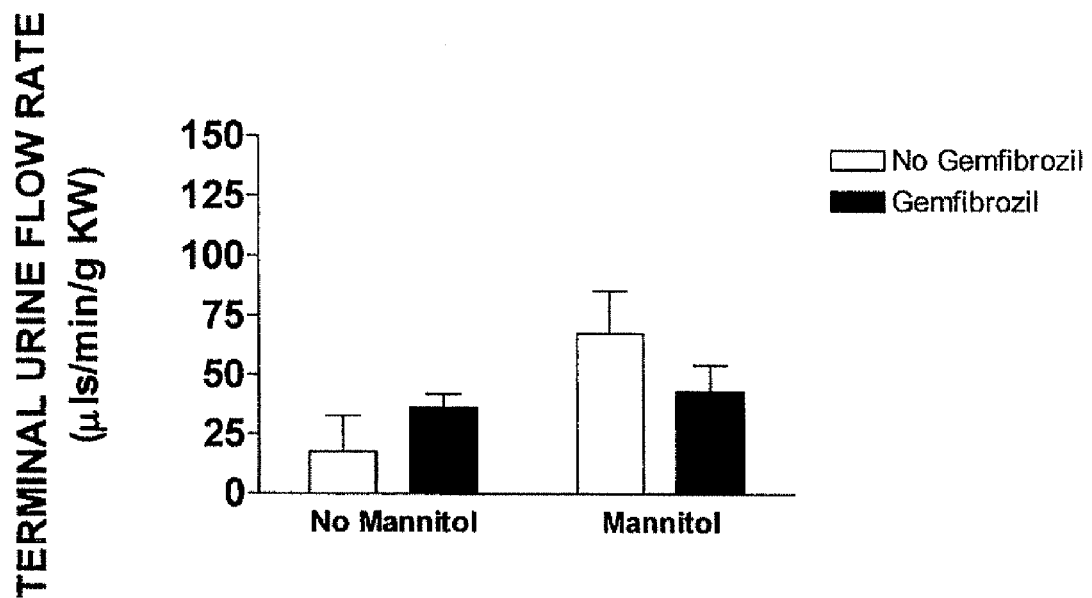
FIG. 4B is a graph of the terminal flow rate in control kidney and kidney exposed to mannitol, gemfibrozil, or mannitol+gemfibrozil.
Figure 4C:
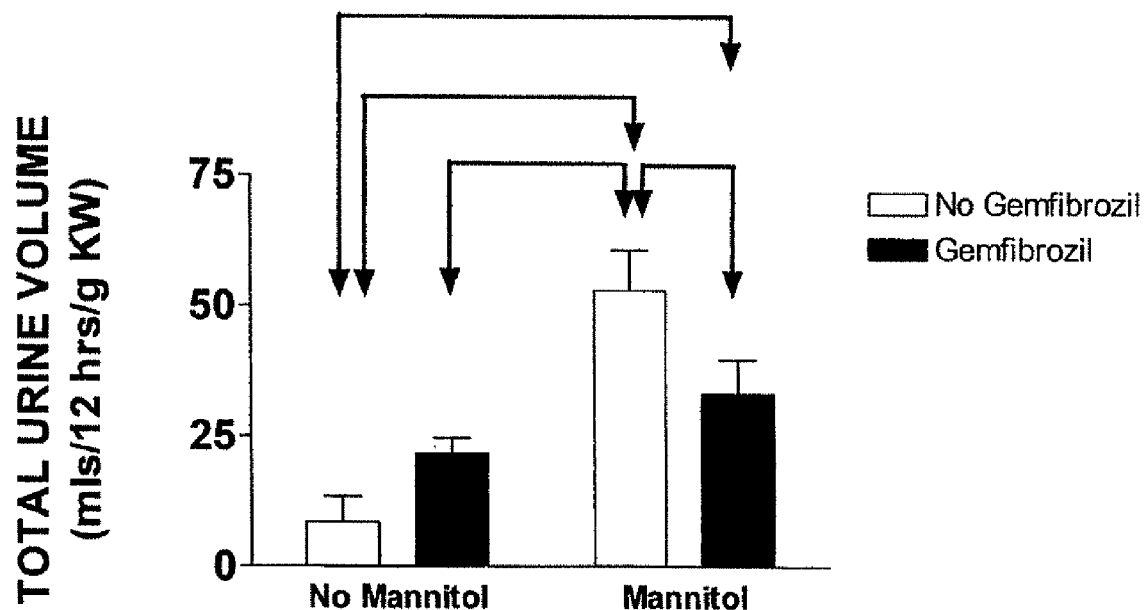
FIG. 4C is a graph of the total urine volume in control kidney and kidney exposed to mannitol, gemfibrozil, or mannitol+gemfibrozil.

FIGS. 4A-4C illustrate the effects of mannitol, gemfibrozil and gemfibrozil plus mannitol on initial urine flow rate (FIG. 4A; "a" indicates statistically significantly different compared with all other groups (Fisher's Least Significant Difference test); interaction term in the 2-factor analysis of variance was p=0.0003), terminal urine flow rate (FIG. 4B) and total urine volume (FIG. 4C; arrows connect statistically significantly different groups (P<0.05 Fisher's Least Significant Difference test); interaction term in the 2-factor analysis of variance was p=0.0223). Both gemfibrozil and mannitol increased total urine volume; however, the diuretic effects of mannitol were greater than those observed with gemfibrozil, and the diuretic actions of gemfibrozil plus mannitol were less than those observed for mannitol per se. Thus, there was a statistically significant interaction between gemfibrozil and mannitol on total urine volume. Similar trends were observed with respect to the initial and terminal urine flow rates; however the interaction did not achieve statistical significance with the terminal urine flow rates and none of the treatments significantly altered terminal flow rates.

Staining for apoptosis with Apoptag revealed diffuse areas of apoptosis in L-15 alone kidneys. Mannitol and gemfibrozil reduced the degree of apoptosis, and the combination appeared to be even more effective in this regard.

An additional three kidneys were perfused with the potent PPARα agonist WY-14643 and compared with the L-15 alone group. At the light microscopic level, histological preservation was improved by WY-14643 compared to L-15 alone. These results extended the findings with gemfibrozil to a structurally different PPARα agonist, thus supporting the conclusion that the preservation effects of gemfibrozil are shared by the pharmacological class of PPARα agonists.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A method for preventing, reducing or reversing organ damage or enhancing organ preservation comprising contacting the organ with a PPARα agonist in an amount effective to prevent, reduce or reverse organ damage or enhance organ preservation, removing the organ from a donor subject's body, and transplanting the organ into a recipient's body, wherein the organ is contacted with the PPARα agonist during the removal of the organ from the donor subject or ex vivo following the removal of the organ from the donor subject.

2. The method of claim 1, wherein the PPARα agonist comprises a fibric acid derivative.

3. The method of claim 2, wherein the fibric acid derivative is selected from the group consisting of gemfibrozil, clofibrate, fenofibrate, ciprofibrate and bezafibrate.

4. The method of claim 1, wherein the PPARα agonist is gemfibrozil.

5. The method of claim 1, wherein the PPARα agonist is 4-chloro-6-(2,3-xylidino)-2-pyrimidinylthioacetic acid.

6. The method of claim 1, further comprising contacting the organ with a cell-impermeable solute.

7. The method of claim 6, wherein the cell-impermeable solute comprises mannitol.

8. The method of claim 7, wherein the PPARα agonist is gemfibrozil.

9. The method of claim 7, wherein the PPARα agonist is 4-chloro-6-(2,3-xylidino)-2-pyrimidinyl thioacetic acid.

10. The method of claim 1 or 6, wherein the organ is selected from the group consisting of kidney, liver, heart, skin and lung.

11. The method of claim 1 or 6, wherein the organ is a kidney.

12. The method of claim 1, wherein the PPARα agonist is delivered into the organ's blood supply while the organ is being perfused by a cardiovascular system.

13. The method of claim 6, wherein the PPARα agonist and cell-impermeable solute are delivered into the organ's blood supply while the organ is being perfused by a cardiovascular system.

14. A method for preventing, reducing or reversing organ damage or enhancing organ preservation comprising contacting an organ with a preservation solution wherein the preservation solution comprises a PPARα agonist in an amount effective to prevent, reduce or reverse organ damage or enhance organ preservation, removing the organ from a donor subject's body, and transplanting the organ into a recipient's body, wherein the organ is contacted with the preservation solution during the removal of the organ from the donor subject or ex vivo following the removal of the organ from the donor subject.

15. The method of claim 14, wherein the PPARα agonist comprises a fibric acid derivative.

16. The method of claim 14, wherein the fibric acid derivative is selected from the group consisting of gemfibrozil, clofibrate, fenofibrate, ciprofibrate and bezafibrate.

17. The method of claim 14, wherein the PPARα agonist is gemfibrozil.

18. The method of claim 14, wherein the PPARα agonist is 4-chloro-6-(2,3-xylidino)-2-pyrimidinylthioacetic acid.

19. The method of claim 14, wherein the preservation solution further comprises a cell-impermeable solute.

20. The method of claim 19, wherein the cell-impermeable solute comprises mannitol.

21. The method of claim 19, wherein the PPARα agonist is gemfibrozil.

22. The method of claim 19, wherein the PPARα agonist is 4-chloro-6-(2,3-xylidino)-2-pyrimidinylthioacetic acid.

23. The method of claim 14 or 19, wherein the organ is selected from the group consisting of kidney, liver, heart, skin and lung.

24. The method of claim 14 or 19, wherein the organ is a kidney.

25. The method of claim 14 or 19, wherein the preservation solution is flushed or continuously perfused or intermittently perfused through blood vessels of the organ.

26. The method of claim 14 or 19, wherein the organ is contacted with the preservation solution during the removal of the organ from the donor subject.

27. The method of claim 14 or 19, wherein the organ is contacted with the preservation solution after the removal of the organ from the donor subject.

28. The method of claim 1, wherein the organ is contacted with the PPARα agonist during the removal of the organ from the donor subject.

29. The method of claim 6, wherein the organ is contacted with the cell-impermeable solute during the removal of the organ from the donor subject.

30. The method of claim 1, wherein the organ is contacted with the PPARα agonist after the removal of the organ from the donor subject.

31. The method of claim 6, wherein the cell-impermeable solute is contacted with the organ after the removal of the organ from the donor subject.

* * * * *